United States Patent [19]

Hein et al.

[11] Patent Number: 5,986,770
[45] Date of Patent: *Nov. 16, 1999

[54] APPARATUS AND METHOD FOR THE OPTICAL CHARACTERIZATION OF THE STRUCTURE AND COMPOSITION OF A LIGHT SCATTERING SAMPLE

[75] Inventors: Heinz-Michael Hein, Seeheim-Jugenheim; Dirk Boecker, Heidelberg; Matthias Essenpreis, Gauting, all of Germany

[73] Assignee: Roche Diagnostics GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,379
[22] PCT Filed: Jul. 27, 1995
[86] PCT No.: PCT/EP95/02967
§ 371 Date: Jan. 30, 1997
§ 102(e) Date: Jan. 30, 1997
[87] PCT Pub. No.: WO96/04545
PCT Pub. Date: Feb. 15, 1996

[30] Foreign Application Priority Data

Jul. 30, 1994 [DE] Germany ................... 44 27 101

[51] Int. Cl.$^6$ ................... G01N 21/47; A61B 5/00
[52] U.S. Cl. ................... 356/446; 356/39; 600/473; 600/476
[58] Field of Search ................... 356/237, 239, 356/338, 343, 429–431, 39; 600/310, 313, 473, 476, 475, 477; 250/341.1, 358.1, 339.2

[56] References Cited

U.S. PATENT DOCUMENTS 4,507,564  3/1985  Shimada ................... 356/431
4,958,083  9/1990  Sakamoto ................... 356/431

*Primary Examiner*—Hoa Q. Pham
*Attorney, Agent, or Firm*—Nikaido, Marmelstein, Murray & Oram LLP

[57] ABSTRACT

Apparatus for the optical characterization of the internal structure and/or composition of a spatially extended, scattering sample comprising an arrangement of one or several light sources and one or several light detectors and a displacement sensor.

30 Claims, 13 Drawing Sheets

Fig.15
Fig.16
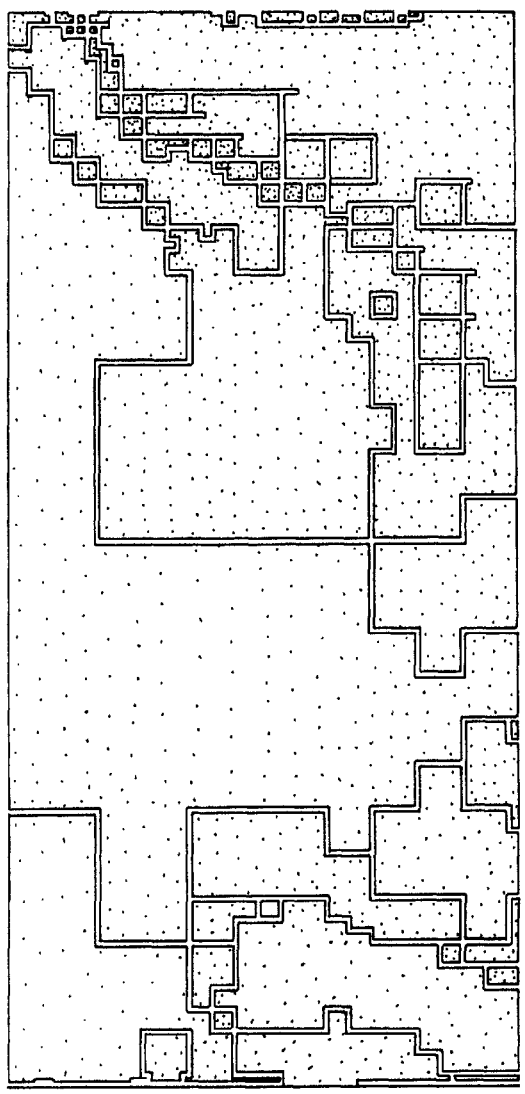
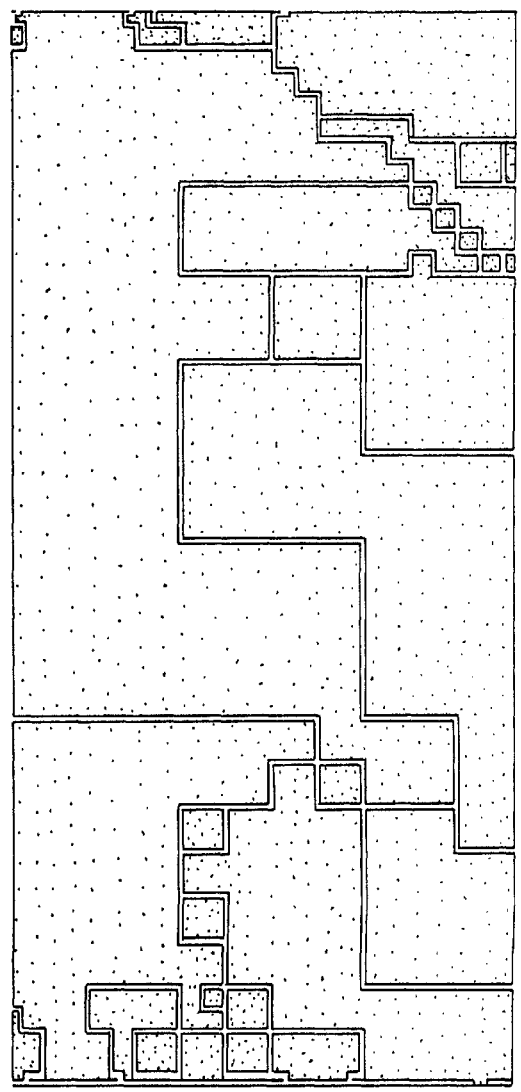

APPARATUS AND METHOD FOR THE OPTICAL CHARACTERIZATION OF THE STRUCTURE AND COMPOSITION OF A LIGHT SCATTERING SAMPLE

BACKGROUND OF THE INVENTION

1. Field of the Invention

Subject matter of the invention is a method for the optical characterization of the internal structure and/or composition of a spatially extended, light scattering sample with the aid of an arrangement consisting of one or several light sources, one or several light detectors, and an apparatus suitable therefor.

2. Discussion of the Related Art

In the field of medical diagnostics, efforts have been made to make use of the internal structures of bodies to recognize diseases. This development began with the exposure of an object to light of a selected wavelength or white light and recording the intensity of the reflected light (Non-invasive methods for the quantification of skin functions; P. J. Frosch and A. M. Klingman (ed.), Springer Verlag Berlin/Heidelberg, 1993, pages 3 to 24 and 25 to 41). A drawback of this method is that it only allows the detection of surface properties as the information is determined by the absorptive or reflective properties of the surface. Another drawback of the method is the poor reproducibility in a quantitative evaluation.

Even scanning devices used to read in a page of text only scan the surface since the light, which is measured and reflected by light source and receiver essentially at the surface due to continuous exposure, must not or cannot penetrate the paper.

The basis for sonographic methods is to distinguish between different structures, e.g. different types of tissue, based on the different reflection factors for sonic waves; said reflection factors being proportional to the acoustic impedance (I. Krestel (ed.), Bildgebende Systeme für die medizinische Diagnostik; Siemens AG, Berlin, München, 2nd edition 1988, page 183 et seq.). Sonographic methods can be used to obtain information from the interior of a sample, but they are entirely dependent on the mechanical properties (density). This means that it is possible to differentiate and represent only structures with greatly varying acoustic impedances. When different soft tissue parts are analyzed, the differences in the acoustic impedance and/or the reflection factor are very small and show either none or only very weak contrasts.

Due to the optical properties of the tissue (scattering and absorption coefficient), the use of light with wavelengths in the near infra-red range (NIR) allows in particular in the field of in-vivo analytics the penetration of thicker tissue areas (some millimeters up to few centimeters) without damage (as is the case with X-rays). In currently known methods various theories are used where the photon path must be mathematically traced back to generate an image based on the measured light intensities; this is accomplished either by the use of measuring methods with a high time resolution (in the ps range) and/or with considerable calculation effort. The measuring apparatus used in these methods generally comprises a high performance, ultra-short pulsed laser, a complex optical unit for laterally scanning the sample surface, and an ultra-fast detector. Possible lasers are, e.g. mode-coupled gas ion laser (Ar, Kr) which synchronously pump dye lasers. Particularly suitable for the detection are streak cameras, microchannel photomultipliers, or Kerr-Shutter (L. Wang et al.: Ballistic Imaging of Biomedical Samples using ps optical Kerrgate; SPIE Vol. 1431, Time Resolved Spectroscopy and Imaging of Tissues (1991), page 97 ff.).

Both handling and costs restrict the use of these apparatus to highly qualified and highly specialized optical laboratories. Equivalent semi-conductor components which can be used for the same type of measurement and allow a necessary degree of miniaturization are presently not available and/or a future availability is not yet in sight. The instrumental difficulties are further complicated by the problem of image reconstruction. Since there are countless ways for the photons to travel from the light source to the detectors, it is not possible to give one unique reconstruction algorithm, as is possible in computer tomography, for example. Although first practical attempts at solving the problem have been made (S. R. Arridge et al.; New results for the development of infra-red absorption imaging; Proceedings of SPIE—The International Society of Optical Engineering, Vol. 1245, pages 92—103), a method for a successful reconstruction has not yet been shown. Moreover, owing to the computing times involved, these methods are not suitable for use in clinical diagnostics.

EP-A 0 387 793 describes a sensor that is placed on a skin section to generate an optical image of the tissue beneath it. However, this apparatus is not suitable for examining larger areas of the body as this would require a very large number of detectors. Moreover, the optical resolution of the generated image is not satisfactory.

DE-A-4341063 describes a method for determining density distributions, wherein the light passing through the tissue is evaluated with respect to the phase and amplitude of high-frequency modulated radiation.

SUMMARY OF THE INVENTION

It was, hence, an object of the present invention to provide an apparatus and/or method that is also suitable to detect the internal structure of light scattering samples in a high local resolution.

Subject matter of the invention is, hence, an apparatus or device for the optical characterization of internal structures and/or compositions of a light scattering sample. The invention comprises an arrangement of one or several light sources and one or several light detectors. The arrangement also comprises a diplacement sensor. Another subject matter of the invention is a method for the optical characterization of these structures.

An apparatus for the optical characterization is an instrument that generates a characterization by emitting light from a light source and detecting the light reflected by the sample on a detector. In accordance with the invention, said apparatus may comprise one or several light sources. Moreover, it is preferred that the apparatus comprise several light detectors.

An optical characterization method includes all measurements that detect a certain property of light which is affected by the internal structure of the sample. This includes, for example, measuring the intensity (weakening the light intensity by absorption and scattering, e.g. corresponding to PCT/DE 93/01058), measuring the degree of polarization of the light (depolarizing light that has been emitted as polarized light by means of scattering processes) or the traveling times of photons (e.g. corresponding to DE-A-43 37 570).

A spatially extended sample is a sample with a two-dimensional surface whose internal structure is inhomogeneous in 3 dimensions. It is preferred to have samples with a minimum of 1 cm in length, 1 cm in width, particularly preferred are samples of 2 to 15 cm in length and 2 to 5 cm in width.

To allow the emitted light to travel through the sample to the detector without direct cross talk of the light source, the sample must scatter the arriving light. In this case, the primary light can penetrate the sample through a boundary layer which surrounds the sample, then propagate in the sample along a light path to emerge again from the sample as a secondary light through a boundary layer that is away from the first boundary layer. The multiple light scatterings described in PCT/DE 93/01058 occur on the light path.

The scattering can occur through the particles contained in the sample, but also as a consequence of other internal structures, such as cell walls. This property of a sample is met in particular by human and animal tissue, especially skin and tissue layers found underneath, preferably up to a depth of approximately 25 mm.

The light source is selected such that it emits light with a known intensity depending on measurement methods selected or a known polarization degree or a known intensity modulation of known phase modulations. The light must also satisfy the aforementioned penetration conditions and be subject to scattering by the sample. In order to determine the optimal wavelength, the expert in the field proceeds as follows:

For the preferred processing of absorbing structures such as blood vessels, wavelengths are selected where the absorbance coefficient of the structure in question is great with respect to the environment, i.e. resulting in a high contrast. A wavelength of approx. 650 nm has proven well for the detection of blood, for example.

For the preferred processing of scattering structures, a wavelength is selected with no or only small specific absorption ranges that could falsify the result as a decrease in the intensity could be a result of highly scattering structures in the light path or be caused by absorption.

For the examination of objects, wavelengths in the ultraviolet visible and infra-red range between 200 and 10000 nm are suitable.

Suitable wavelengths for the examination of human skin are those in the range between 400 and 2500 nm. Particularly preferred wavelengths are those in the range between 400 and 1300 nm. Light sources to generate a light of such a wavelength are known to the expert. Particularly suitable sources are laser diodes or LEDs as they are so small that several light sources can be arranged on the relatively small surface of the apparatus.

Particularly suitable light detectors are photodiodes or CCDs as they can be arranged in a narrow design.

A displacement sensor is a component which traces the path covered on the surface of the sample when the apparatus is in motion and then feeds this information to a control unit. Such displacement sensors are principally known to the expert.

Suitable instruments are mechanical instruments that work with angle encoding. When linear displacements are to be sensed, drum-type sensors are preferred. If a non-linear displacement is to be sensed, spherical sensors as they are known from a mouse for controlling a PC are suitable. These displacement sensors are used to assign each value measured at a light detector to a certain measuring site.

In a preferred manner, an arrangement of the invention for a linear detection has at least two drums which are located before and after the light sources and the light detectors in direction of movement. On the surfaces, these drums are provided with a material to prevent sliding of the drum on the sample surface. In a preferred manner, the drums have a rubber surface. Moreover, when elastic samples, e.g. tissue, are to be analyzed, it is preferred that the surface of the drums extend 0.1 to 5 mm, particularly preferred 0.5 to 2 mm, over the surface of the apparatus facing the sample, said surface containing the light sources and the light detectors. This distance ensures that there is no space left between the surface of the apparatus and the surface of the sample when the apparatus is pressed onto the human skin. In this arrangement, interferences resulting from the reflection of the light emitted on to the surface of skin and/or from radiation directly emerging from a light sensor on to a detector are avoided as best as possible.

The assignment of the measured values (intensity to site of measurement) is carried out in an electronic evaluation unit. The values can be stored in a memory unit and be called up, if necessary. An intensity profile can then be established for each pair of light source/light detector based on the total of all measured values for the measurement sites located on the path covered. If several pairs of light source/light detectors are evaluated, light detectors that are not located on the same path generate additional intensity profiles which describe the inner structure of the sample between light source and light detectors. The use of numerous large detectors, therefore, produces a 3-dimensional picture if the intensity is plotted in dependency on the covered path and the site of detection.

In addition to mechanical displacement sensors, it is also possible to employ optical displacement sensing methods or mathematical methods.

By applying a regular bright/dark pattern with known dimensions on the sample, it is possible to clearly identify the site by measuring the bright and dark zones comparable to a barcode reader. This can be achieved either by using additional detectors located outside the actual measuring field, or the pattern can be recorded directly with a measurement provided said pattern is applied directly on the sample or by means of a transparent carrier for the wavelength.

A mathematical method of sensing the displacement is the use of several identical measuring pairs. They are arranged such that they cover the same site when the apparatus is moved in a given direction. They, hence, measure the same intensity profile but at different times and in dependency upon the speed of movement. With a given distance between these two measurement pairs, the speed and, hence, the site can be measured while the time is known by establishing a time correlation between these two curves.

In the apparatus of the invention, the geometry of the arrangement of light sources, light detectors and displacement of sensor during the measurement is preferably constant. Principally, the arrangement can comprise only one single light source with a corresponding light detector so that an intensity profile I can be generated as a function of the site as stated above. In a second variant, only one light source but several detectors are used. Said detectors are located either at different distances to the light source and/or different angles between light source/detector and direction of movement.

BRIEF DESCRIPTION OF THE DRAWINGS

FIGS. 15 and 16 are two-dimensional intensity distributions of a skin portion in gray values.

DETAILED DESCRIPTION OF THE PREFERRED EMBODIMENTS

In the preferred case, the arrangement of the invention comprises several light sources and several light detectors. In order to carry out a measurement, it is preferred to activate only one light source at a given time. This source detects the amount of light arriving at one detector or several detectors. If several light sources are activated at the same time, it must be ensured that the amount of light detected by one detector is emitted essentially by one light source, said amount being preferably 90%, preferably more than 99%. This also applies to the influence of foreign light sources, e.g. daylight or other sources of illumination. The activation times of the light source should therefore be timed. With the activation timing being known, it is possible to have a better assignment of activated light source and detectors to be read during this cycle time. During a measurement, it is preferred that the cycle times be identical and constant. The activation times, or inversely the pulse frequencies, depend on the desired maximum speed of movement, the local resolution in direction of movement as well as the number of light sources and detectors which must be switched on and read for given speed of movement in the given local resolution in direction of movement. During manual operation, appropriate speeds of movement range between 1 and 20 cm/s. When the apparatus of the invention is used together with mechanical support means for controlling the movement (e.g. motors) it is possible and expedient to have significantly higher or lower speeds depending on the local resolution. During manual operation, pulse frequencies, e.g. for 16 light sources and 16 detectors, range between 10 MHz and 1 kHz, preferably between 1 MHz and 20 kHz. The resulting resolutions in direction of movement are below 0.1 mm, i.e. below the size of the structures in question.

In an advantageous embodiment, light sources and light detectors are arranged in pairs, with each pair consisting of one light source and one light detector. The light sources and light detectors of each pair are located on an assumed line that is essentially perpendicular to the direction of movement of the arrangement (cf. FIG. 1).

Figure 1:
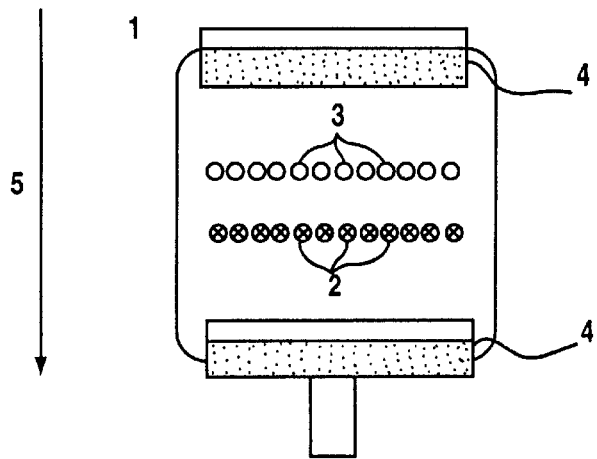
FIG. 1 illustrates an embodiment of the present invention.

According to FIG. 1, the light sources are preferably activated at different times and the amount of light arriving at a given detector is detected. The activated light source and the detector associated with it form one pair.

In a preferred manner, the distance between light source and light detector of each pair and the angle between light source detector and direction of movement are the same. For the preferred samples and light characteristics, a distance d of 1 to 50 mm, particularly preferred 2.5 to 20 mm, has proven to be advantageous.

Light source and light detector of each pair are preferably located at the same boundary of the sample, i.e. the reflection is measured. However, as soon as two opposite boundaries of the sample are accessible, it is also possible to measure the transmission whereby light source and light detector are located on opposite boundaries of the sample. The terms transmission and reflection used with respect to the diffuse characteristics of the secondary light must not be understood to mean that the secondary light emerges from the sample with a highly dominating preferred direction.

In the figures, the lengths and distances X and Y are indicated in millimeters. The intensities I are given in relative units.

Arrangement 1 shown in FIG. 1 shows in addition to the light sources 2 and light detectors 3 also two drums 4 of which at least one serves as a displacement sensor. This arrangement is therefore suitable for sensing several linear intensity profiles corresponding to the paths covered by the detectors in direction of movement 5.

In addition to this arrangement, the apparatus in accordance with the invention also comprises additional components that are advantageous for its use. It must be taken into consideration that these components can be connected to each other either in a rigid or flexible manner, but also via communication pathways. To ensure proper functioning, the resulting one-piece or multi-piece apparatus should comprise an electronic control unit for light sources and detectors, an amplifier, a display, a recorder or an analog-to-digital converter, and a computer for further processing the generated data in addition to the described arrangement of light sources, light detectors and displacement sensor. In a preferred manner, all the aforementioned components with the exception of arrangement 1 are included in a footed instrument whereas arrangement 1 comes as a relative small handy instrument. The connection between these two elements can be accomplished either mechanically via flexible cables or electromagnetic radiation.

Figure 2:
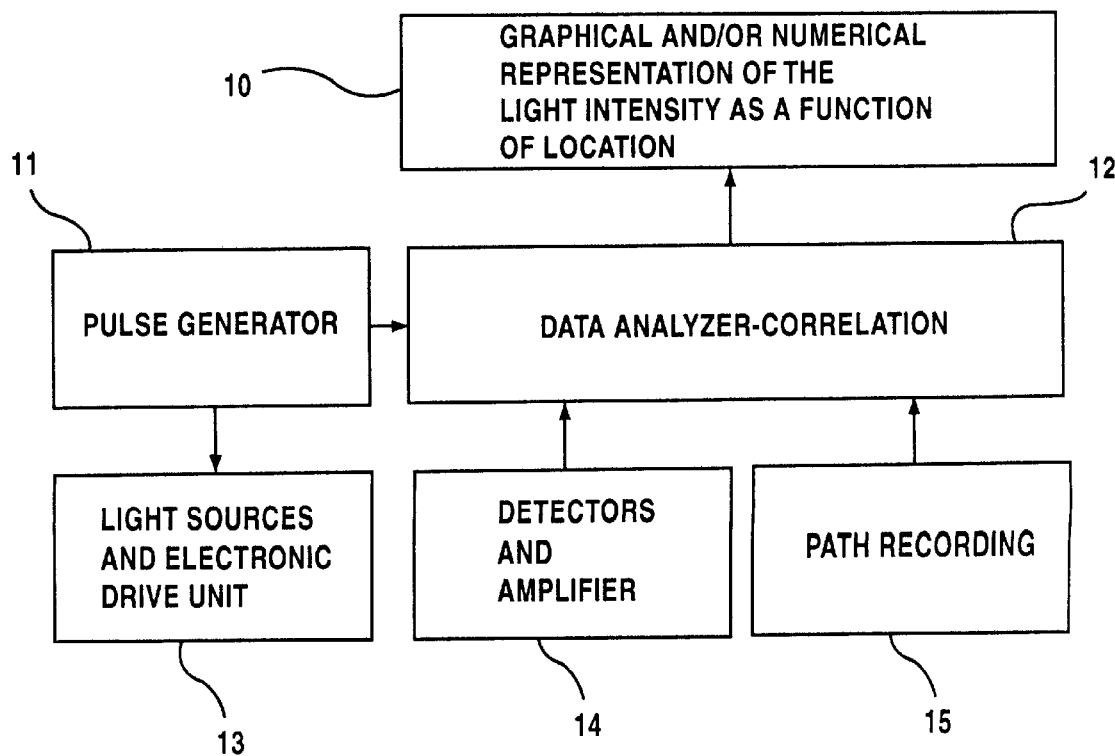
FIG. 2 is a block diagram of the structural elements of the invention.

FIG. 2 is a block diagram of the structure in accordance with the invention.

Figure 3:
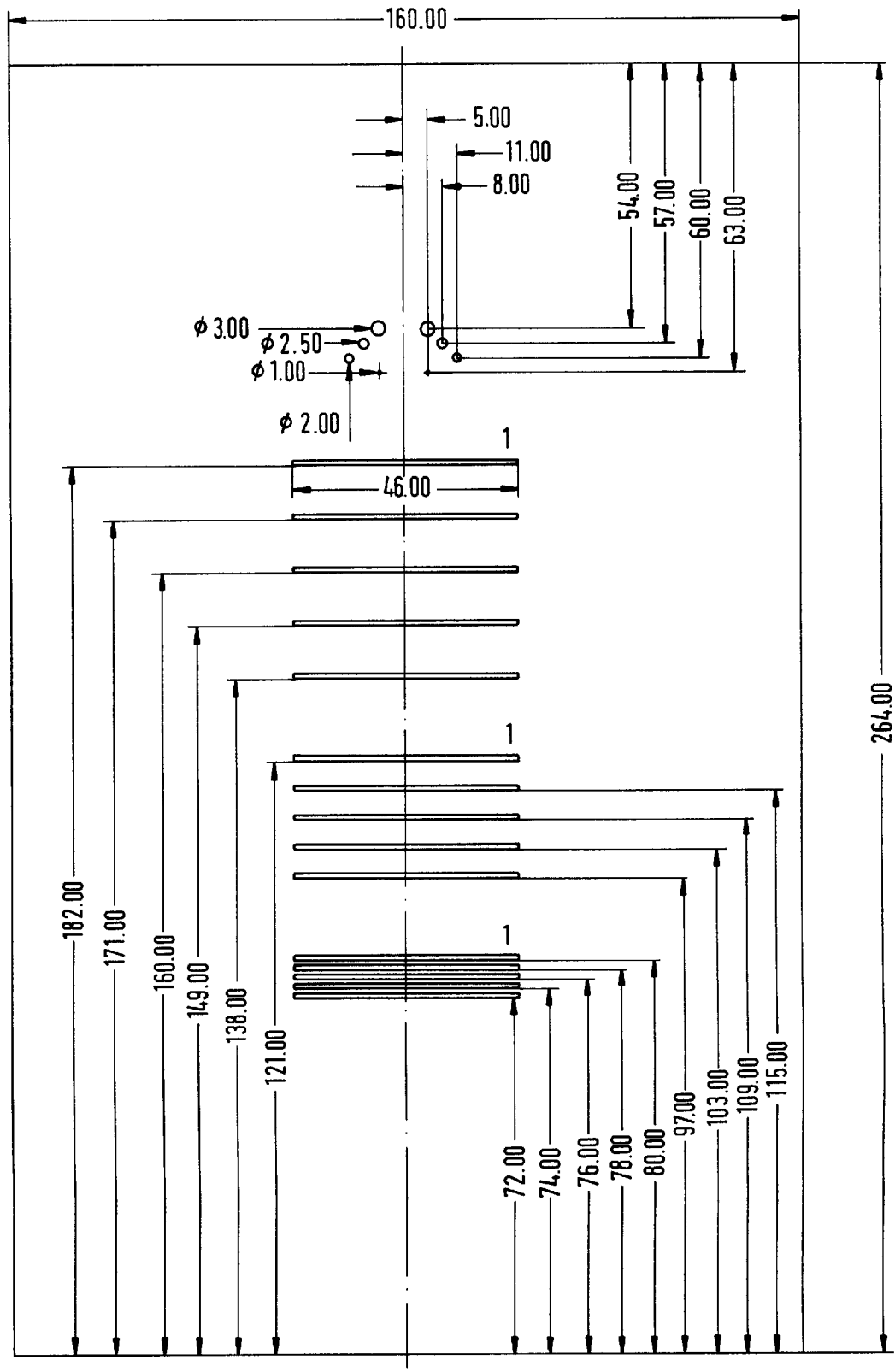
FIG. 3 describes a scattering test object for the present invention.

FIG. 3 describes a test object made of a scattering material (thickness approx. 20 mm, made of Teflon) in which there are mechanical inhomogeneities in the form of defined recesses (depth 4.5 mm (1) or 2.5 mm (rest)) at different distances.

Figure 4:
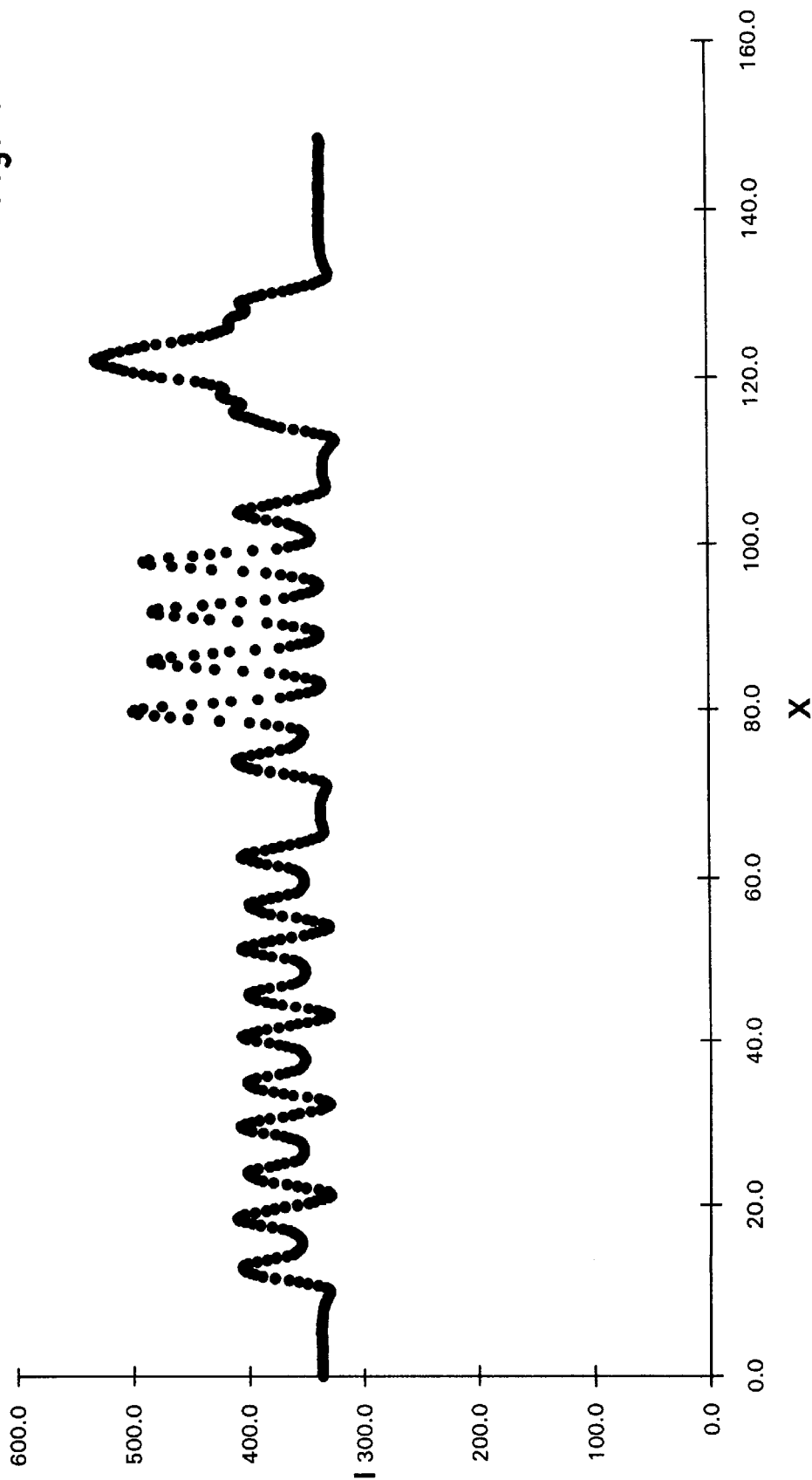
FIG. 4 illustrates a one-dimensional intensity profile of the test object of FIG. 3.

FIG. 4 shows a one-dimensional intensity profile I as a function of the site. The profile was generated by measuring the test object described in FIG. 2 with the aid of the apparatus in accordance with the invention. The distances between light source and detector were approximately 7 mm.

Figure 5:
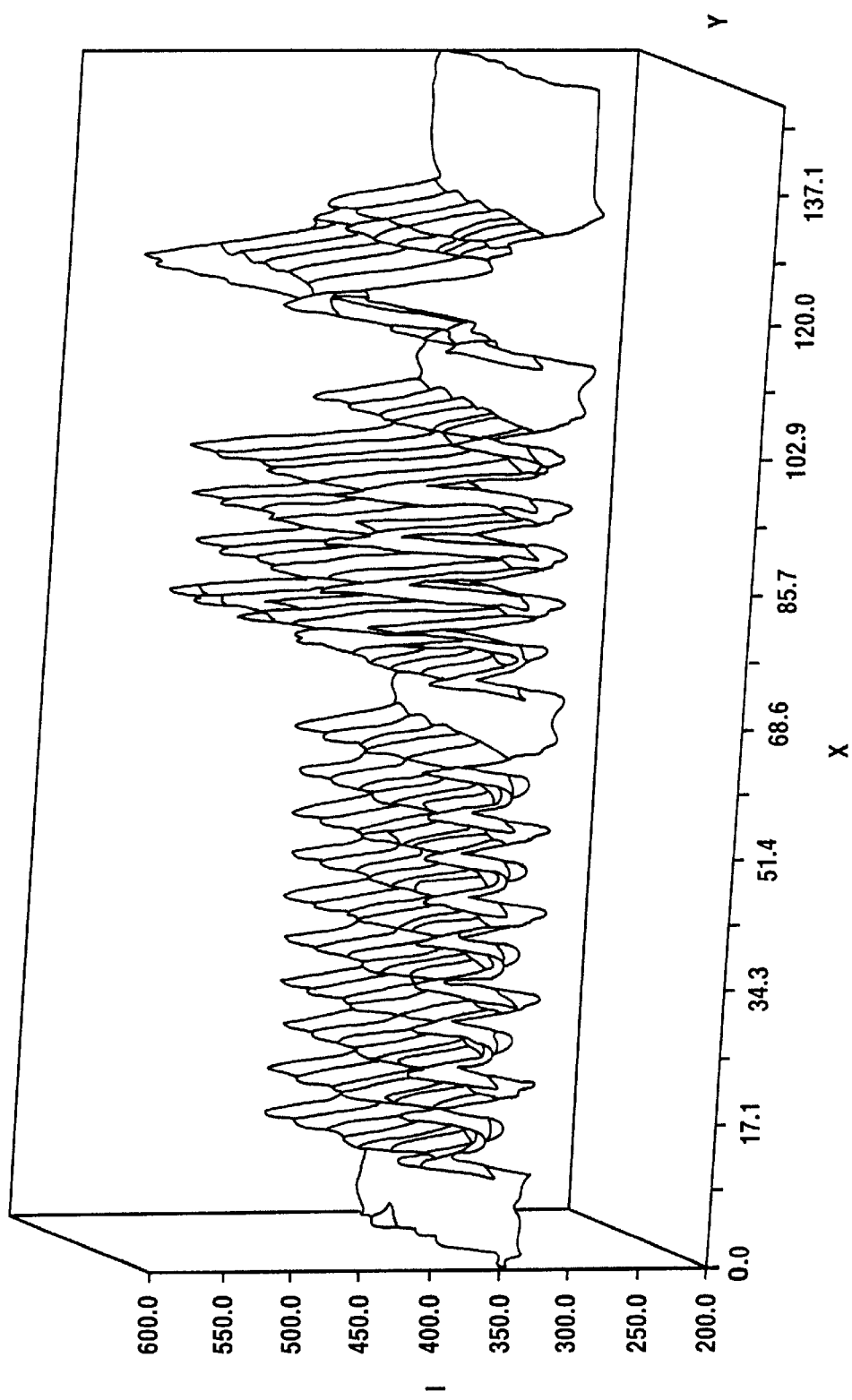
FIG. 5 illustrates a two-dimensional intensity profile of the same test object.

FIG. 5 shows a two-dimensional intensity profile that was generated with the same test object. The apparatus used to develop the profile of FIG. 5 included fourteen sources and fourteen detectors corresponding to arrangement A in FIG. 6 with a distance d of 7 mm. Other quantities of light sources and detectors could be used, and still be within the spirit and scope of the invention.

Figure 6A:
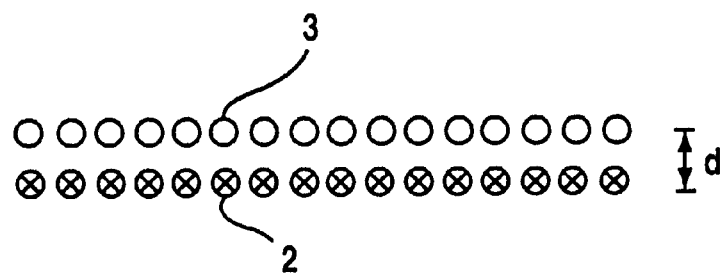
FIG. 6 illustrates variations of light source/detector arrangements according to the present invention.
Figure 6B:
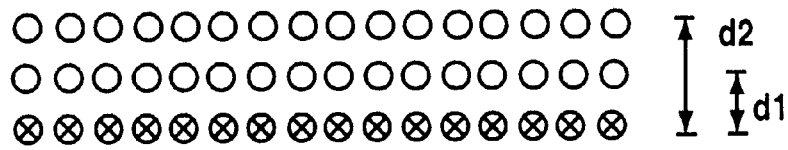
Figure 6C:
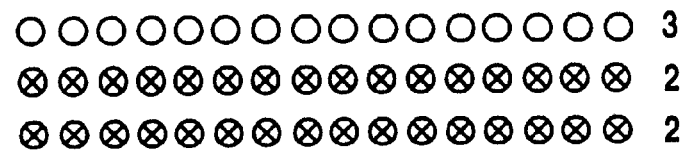

FIG. 6 shows three possible variants for arranging light sources/detectors. In arrangement A, both light sources (2) and light detectors are arranged on an assumed line. The distance between the two lines is identified with the letter d. In arrangement B, an evaluation for two different distances d1 and d2 is made possible in that a second row of light detectors is provided. The same effect can be achieved by using two rows of light sources and only one row of light detectors (arrangement C).

Figure 7:
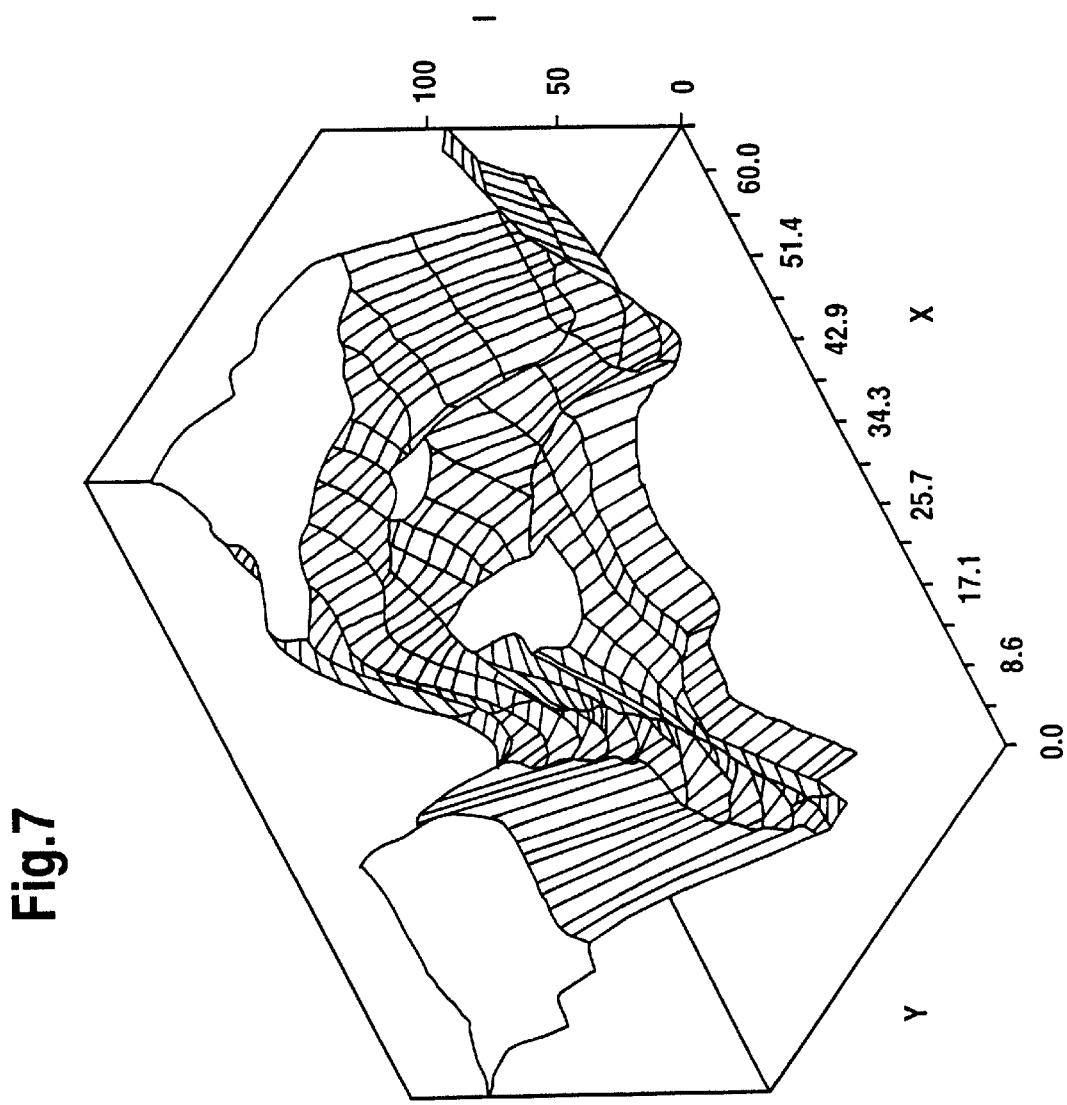
FIG. 7 illustrates a two-dimensional representation of an intensity profile utilizing an apparatus according to the invention.

FIG. 7 is a two-dimensional representation of the intensity as a function of the covered paths and the light source/detector position. It was obtained on human skin with an apparatus according to FIG. 1. The figure shows the intensity profiles of 14 detectors over a path of 60 mm. The location of a vein (low intensity, dark spots) can be clearly identified.

As the light property is measured in terms of reflection after traversing the sample, the two-dimensional intensity profile is determined by parameters which affect the optical properties of the object to be examined.

The so measured intensity of profiles which first allow only a relative association can be used to clearly determine the inner structure of a given area in that the site of the start or the end of a measurement on the sample is recorded. It is thus possible to associate the relative intensity measurement with certain sites on the sample. Advantageously, an origin of coordinates is defined on the apparatus for the exact identification of the various directions of movement. Advantageously, this is the position of the light sources or the detectors.

Another subject matter of the invention is a method for the optical characterization of the inner structure and/or a composition of a spatially extended, scattering sample. The apparatus comprising one or several light sources and one or several light detectors is moved across the spatially extended sample. The movement of the arrangement consisting of light sources and light detectors is advantageously recorded via a displacement sensor. During the movement of the apparatus, the light arriving at the light detectors is detected and the generated signal is recorded. In order to associate the measured signals with given sites on the sample, the measured intensity is correlated with the covered path. This is advantageously done with the aid of a computer. The resulting intensity profiles can be represented either numerically or graphically.

Figures 8A, 8B, 8C:
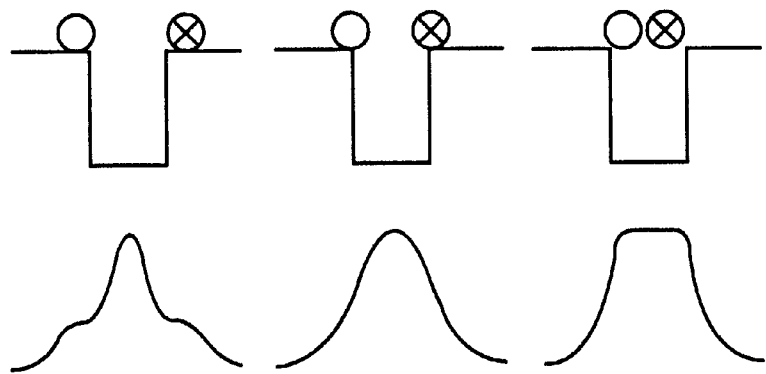
FIG. 8 illustrates various intensity/distance relationships.

The distance d between light source and light detector also affects the possible resolution accuracy. FIG. 8 shows examples of intensities for cases where the distance d is larger than the inner structure; where d is approximately the same as the inner structure; and where d is much smaller than the inner structure. In this case, the inner structure is a gap in the surface of a sample across which the arrangement is moved. By using different wavelengths and/or light source/detector distances, it is possible to prefer certain penetration depths, and increase the specificity for certain components. When vessels are examined, a suitable wavelength is one where hemoglobin shows an absorption. Parts with numerous vessels then show a higher absorption which leads to a lower measured light intensity at the light source/detector pairs above the vessel.

Figure 9:
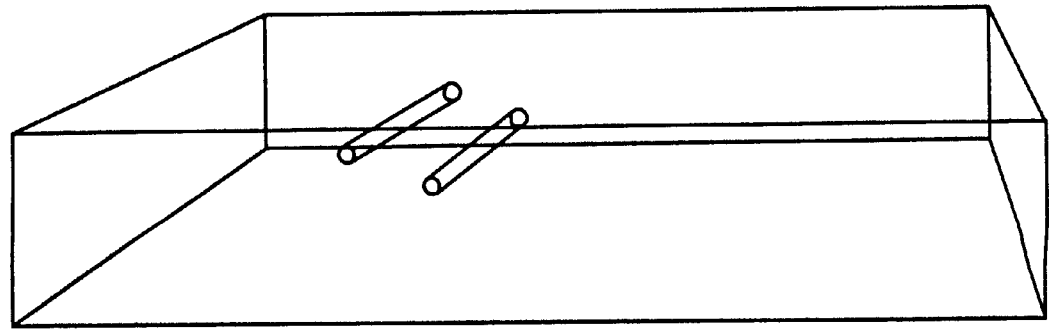
FIG. 9 illustrates a scattering block used in a method according to the present invention.

FIGS. 9 to 13 show the method of the invention as used in another detailed embodiment. A scattering block made of plastic was provided with absorbing structures of different depths and filled with an absorbing medium to simulate absorbing blood vessels in the tissue. The bores have a diameter of 1 mm and are parallel to the surface at a distance of 2.8 and 5.0 mm to the surface, and at an approximate length of 20 mm (FIG. 9).

Figure 10:
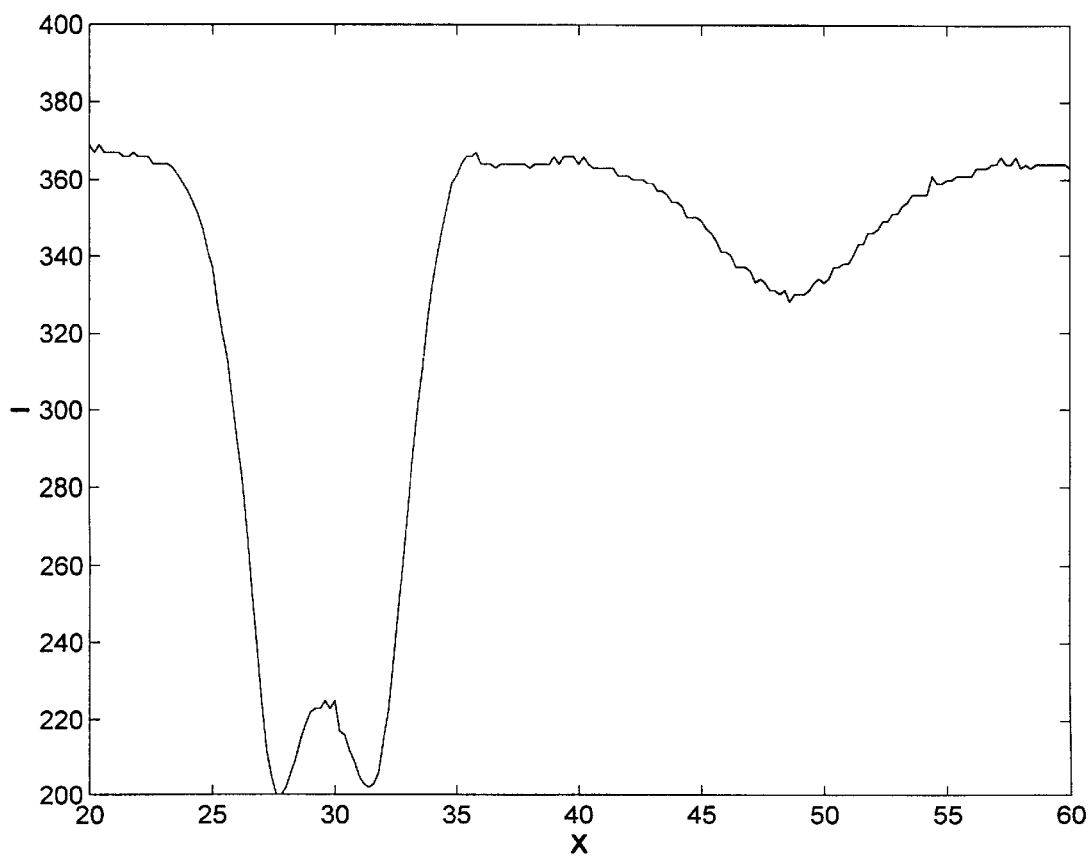
FIGS. 10–13 illustrate intensity/path curves, signal development, and intensity profiles.
Figure 11:
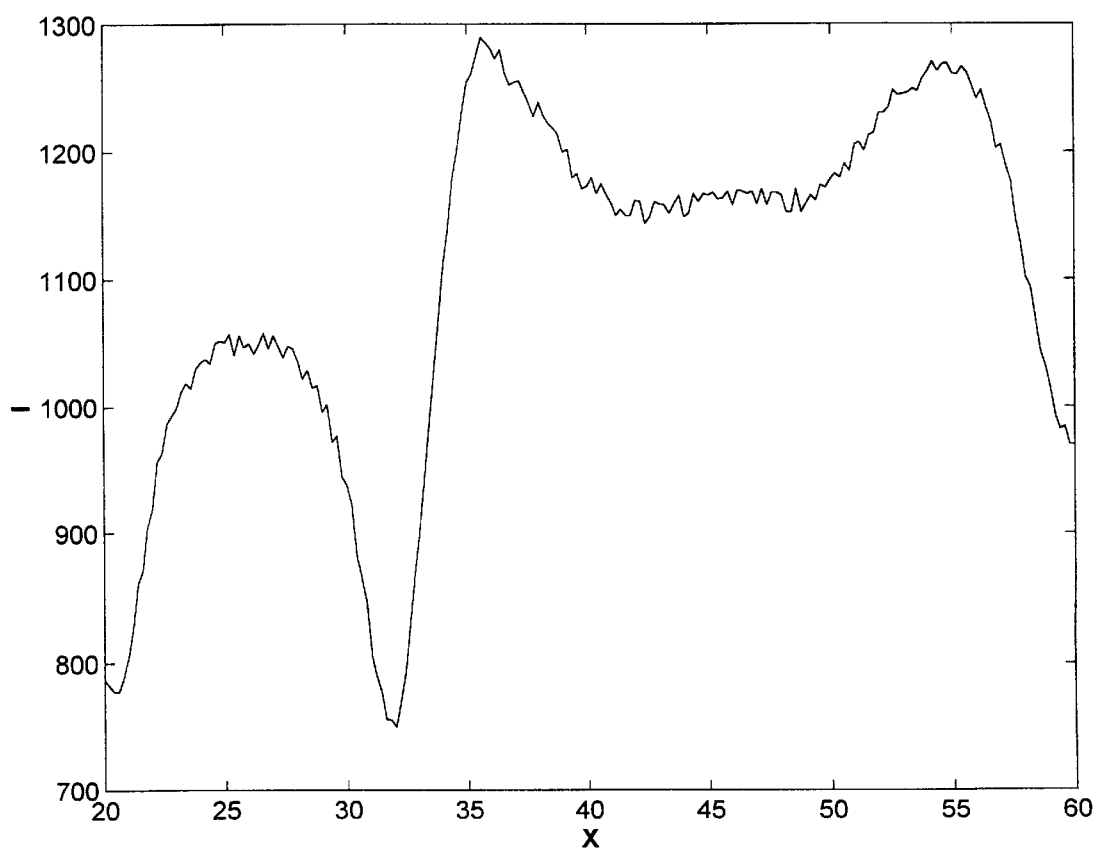
Figure 12:
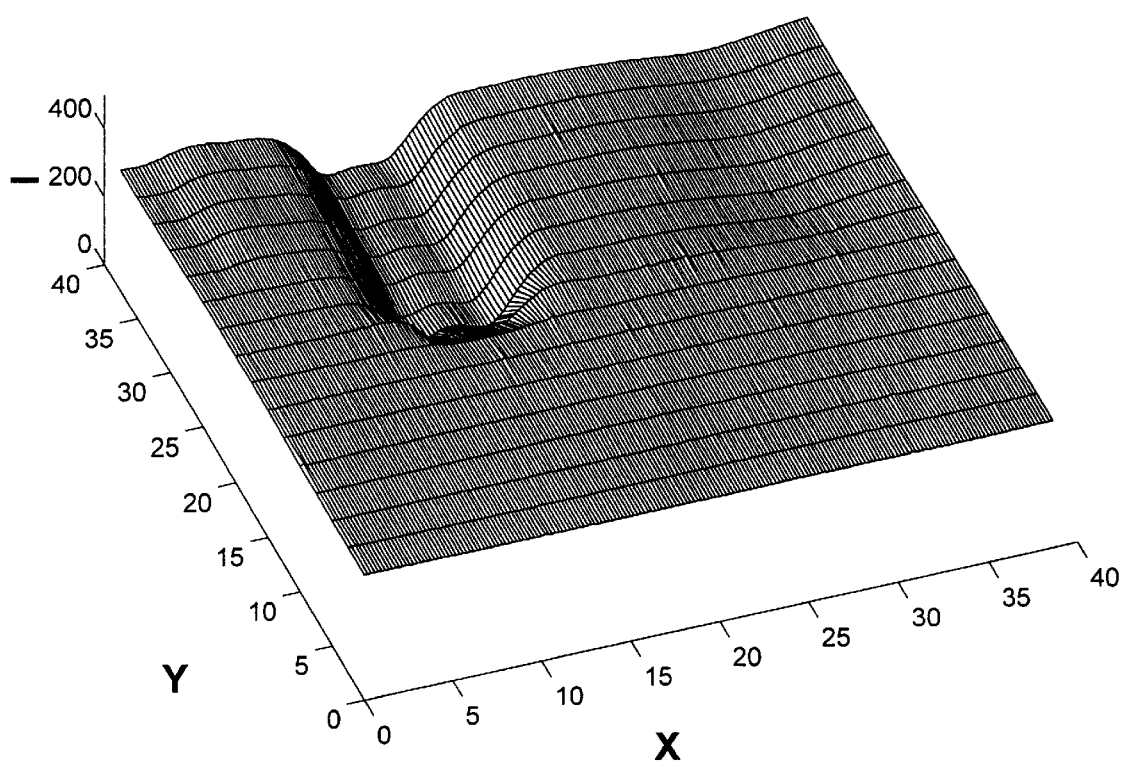
Figure 13:
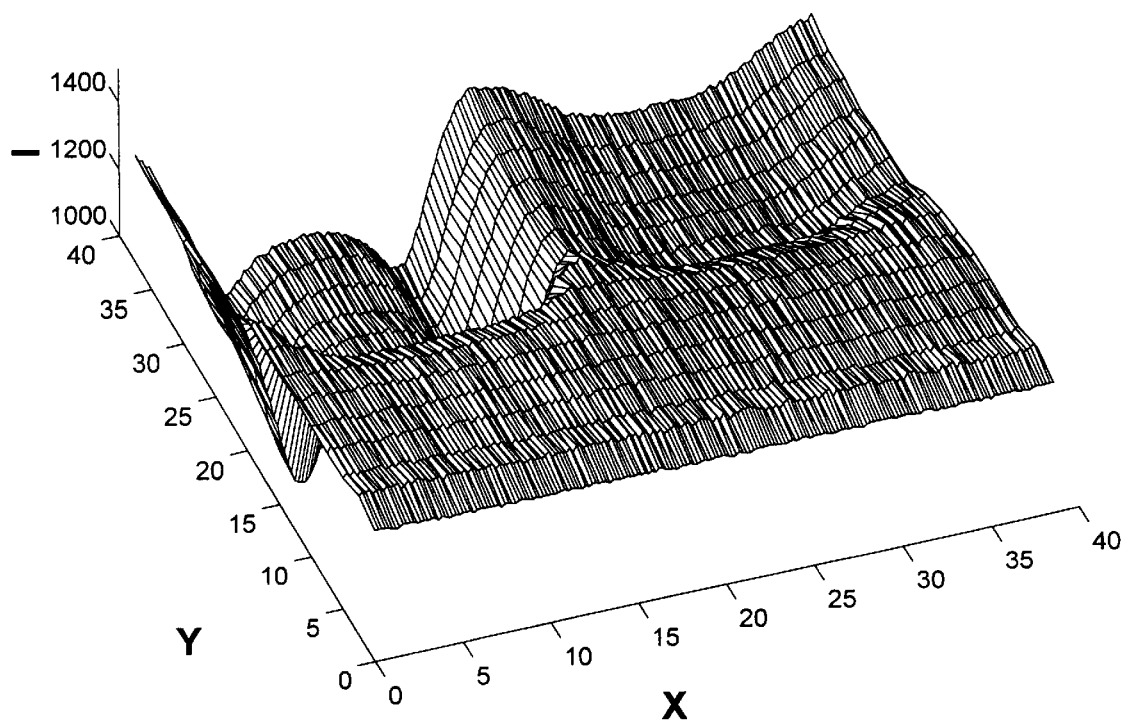

Because of the form of the intensity/path curves, it is possible to provide data on the length, depth and shape of the structures. FIG. 10 shows the intensity/path curve for a selected light source/detector pair with a distance of 7 mm. FIG. 11 shows the signal development for the same light source, however, for a detector at a distance of 14 mm. The signals at 25 mm and 50 mm of path traveled correspond to bores with a depth of 2.8 and 5.0 mm, respectively. The size and depth of the absorbing bores can be concluded from the different forms of the signals. Structures that are close to the surface shows deep signal decrease for a small light source/detector distance, and the lower structure is shown as a relatively weak and broad signal decrease. FIGS. 12 and 13 show the intensity over the entire width of the scanned area for a distance of 7 mm and 14 mm, respectively, between light source and detector.

Figure 14:
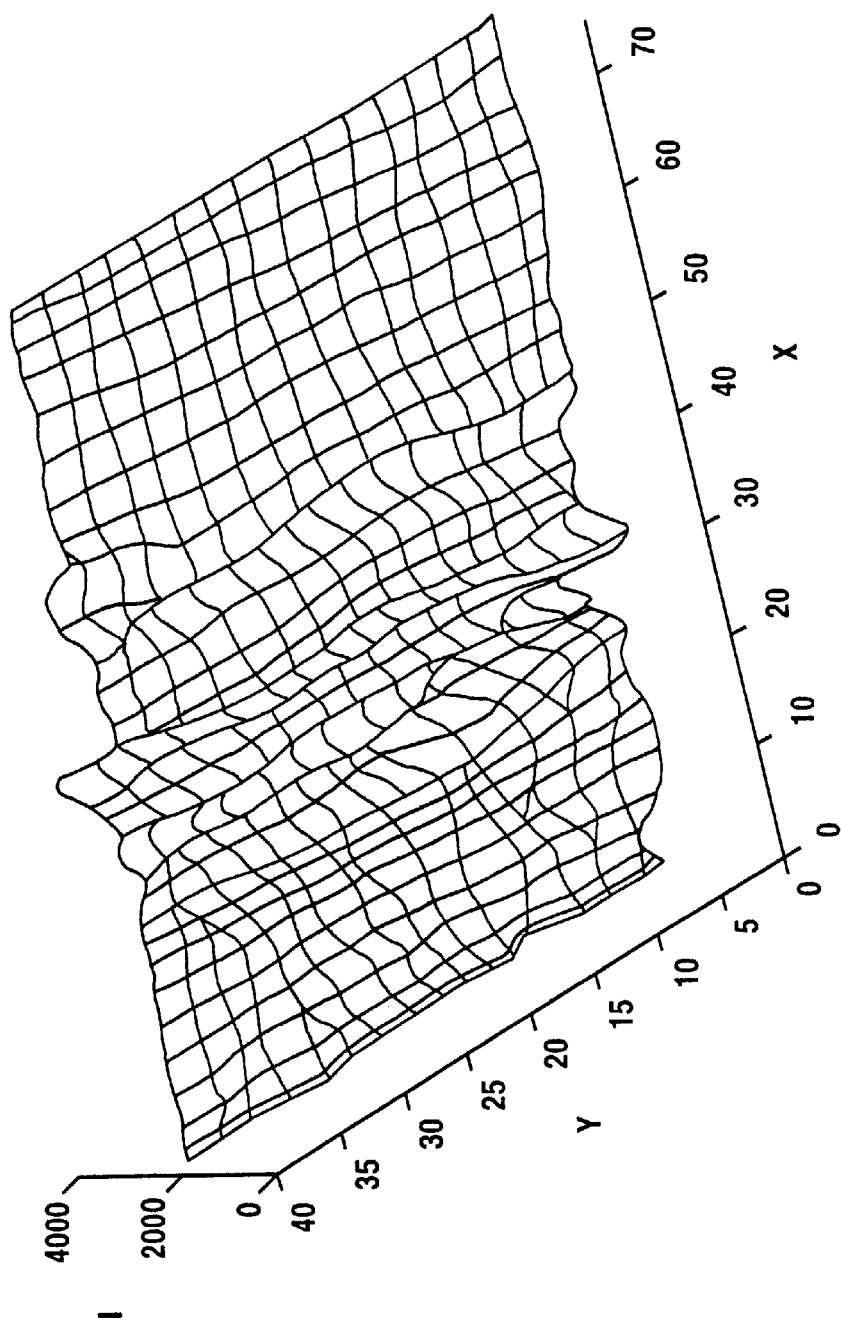
FIG. 14 illustrates an intensity profile showing damage to connective tissue.

FIG. 14 shows that the method of the invention is also suitable for in-vivo measurements. FIG. 14 shows the measurement of damage to connective tissue caused by overstretching (striae). The plotted diagram shows the reflected intensity or a light source/detector distance of 7 mm as a function of the path. Strip-like alterations of the skin running perpendicularly to the scanning direction can be seen between 0 and 15 mm path and after 100 mm. The path between 50 and 100 mm shows normal tissue. Instruments in accordance with the invention can be used for both the documentation of such findings and their control during therapy. As opposed to a mere visual evaluation, the intensity profiles shown also allow an evaluation of the course and the extent of tissue alterations inside the skin in a non-invasive manner.

FIG. 15 shows that the method of the invention can also be used to evaluate the homogeneity of tissue. In order to determine the optical properties of the skin, it is important to evaluate the examined sites with respect to homogeneity since it is not a defined site, but a vaguely defined volume that is measured due to the scattering character of the skin. The derived optical values are, hence, mean values of this volume. It is, therefore, necessary to know the homogeneity of the tissue area examined to exclude false mean values that may have been caused by inhomogeneities.

FIGS. 15 and 16 show the measured two-dimensional intensity distribution of a skin portion in gray values. In FIG. 15, the light source detector distance was 7 mm; in FIG. 16, the distance was 14 mm. The area of skin examined can be further divided in areas of similar intensities by further processing the data, one possibility being the zone growth method. In this method, a freely selected intensity value of the two-dimensional data structure I(x,y) is in a first step compared to the adjacent value I(x+1, y+1), I(x, y+1), I(x−1, y+1), and so forth. Those adjacent values which fulfill a given comparison criterion, e.g. ranging within a certain value range together with the first point, form one area. The result is a first area with similar intensity values. To determine further areas, another starting point outside the already determined area or zone must be determined and the above-described comparison procedure is repeated. As opposed to measurement on the boundary of the areas shown, it is advantageous to measure the optical properties within such defined areas. Moreover, a comparison between FIGS. 15 and 16 shows that when different light source detector distances are present, the examined tissue has different homogeneous areas.

Another subject matter of the invention are advantageous applications and uses of the apparatus and the method of the invention. The following are possible examples:

Determining a time-related alteration of a sample, e.g. before and after surgery or during the healing process. The reproducibility of the intensity profiles also allows long-term examinations, e.g. during pathogenic alterations of the skin or controlling the size of skin alterations (moles, birthmarks). In addition, the method is also suitable to examine foreign bodies included in the skin.

Classification of different skin types. In this case, the use of discriminance analyses for establishing different types and associating individual samples to these types is advantageous.

The good local resolution in direction of movement is particularly suitable to derive values from the intensity/path profiles in mathematical operations to successfully identify certain skin areas. It is, for example, possible to determine characteristic, periodically repeated properties of the tissue types via Fourier transformation of the intensity profile for the individual tissue types followed by a discriminance analysis.

Scanning of sites or homogeneity locally or in a time-related manner. Tissue, in particular human skin, is locally inhomogeneous because of structures therein or therebelow. Some parts of the body may be more or less suitable for diagnostic purposes. There are parts that are well or less well suited for a measurement, in particular in case of a non-invasive determination of analyte concentrations in certain tissue parts, e.g. in case of a non-invasive determination of the glucose concentration, according to PCT-DE 93/01058 or U.S. Pat. No. 5,028,787. With the present invention, well-suitable measurement sites can be determined and labeled. This is also advantageous if the non-invasive measurement instrument must be removed from the sample between two measurements and later be attached again. The method of the invention is also suitable to determine the size and/or time-related changes to homogeneous areas of the sample.

The above-described methods can also be applied to non-biological samples. With the apparatus of the invention it is possible to examine material in scattering media without damage. This includes homogeneity tests for plastics and examining molded pieces with structures below their surface.

List of Reference Numerals (1) Arrangement in accordance with the invention
(2) Light sources
(3) Detectors
(4) Drums
(5) Direction of movement
(10) Graphical and/or numerical representation of the light intensity as a function of location
(11) Timing pulse generator
(12) Electronic data analyzer, correlation of path and light intensity
(13) Light sources and electronic drive unit
(14) Detectors and amplifier
(15) Path recording

We claim:

1. An apparatus for in-vivo optical analysis of internal structures of a specimen of light scattering tissue by moving said apparatus relative to a surface of the specimen, said apparatus comprising:

at least one light irradiating means for irradiating primary light into the surface of an in-vivo specimen;

at least one light detecting means for detecting secondary light from the surface of the specimen; and displacement sensor means for sensing a relative movement between the light irradiating means and the light detecting means relative to the surface of the specimen, said displacement sensor means tracing a path on the surface of the specimen and sensing displacement when the apparatus is moved on the surface of the specimen; and evaluation means connected to said light irradiating means, said light detecting means, and said displacement sensor means, said evaluation means processing data from said light detecting means and said displacement sensor means, and correlating the relative movement with said data from said light detecting means.

2. An apparatus as recited in claim 1, further comprising display means connected to said evaluation means, for displaying an optical image generated by the evaluation means thereupon.

3. An apparatus as recited in claim 1, wherein said displacement sensor means is coupled to said light irradiating means and said light detecting means.

4. An apparatus as recited in claim 1, wherein said evaluation means also generates an optical image from the data which is processed from the light detecting means and the light displacement sensor means.

5. An apparatus as recited in claim 1, wherein said evaluation means generates a one-or-more dimensional intensity profile from said data.

6. An apparatus as recited in claim 1, wherein said evaluation means generates a classification of a specimen type based upon the data process from the light detecting means and the displacement sensor means.

7. An apparatus as recited in claim 1, said apparatus comprising a plurality of light irradiating means.

8. An apparatus as recited in claim 1, comprising a plurality of light detecting means.

9. An apparatus as recited in claim 1, comprising a plurality of light irradiating means and a plurality of light detecting means, wherein each of said plurality of light irradiating means is paired with a corresponding one of the plurality of light detecting means.

10. An apparatus as recited in claim 9, wherein corresponding light irradiating means and light detecting means are separated by a same distance as other corresponding light irradiation means and light detection means.

11. An apparatus as recited in claim 10, wherein said same distance is between 0.5 mm and 100 mm.

12. An apparatus according to claim 9, wherein said plurality of light irradiating means and said plurality of light detecting means are disposed in a coplanar configuration.

13. An apparatus as recited in claim 1, wherein said light detecting means detects light intensity.

14. An apparatus as recited in claim 1, wherein said light detecting means detects a degree of polarization of the secondary light.

15. An apparatus as recited in claim 1, wherein said light detecting means detects a travel time of photons from the light irradiation means to the detecting means.

16. An apparatus according to claim 1, wherein said at least one light irradiating means and said at least one light detecting means are disposed in a coplanar configuration.

17. A method for in-vivo optical analysis of internal structures of a specimen of light scattering tissue, said method comprising the steps of:

irradiating primary light into a surface of a scattering in-vivo specimen with a light irradiating means;

detecting secondary light emerging from the surface of the specimen with a detecting means;

displacing said light irradiating means and said detection means relative to the surface of the specimen;

sensing a displacement of said light irradiating means and said light detecting means with respect to the surface of the specimen with a displacement sensor means, said displacement sensor means tracing a path on the surface of the specimen and sensing displacement when the displacement sensor means is moved on the surface of the specimen;

processing data from the light detecting means and the displacement sensor means; and correlating the data from the light detecting means and the displacement sensor means.

18. A method according to claim 17, comprising a further step of generating an optical image from the correlated data.

19. A method according to claim 17, further comprising a step of generating a one-or-more dimensional intensity profile of the specimen based upon the correlated data.

20. A method according to claim 17, further comprising a step of classifying a sample type based upon the correlated data.

21. A method according to claim 17, further comprising a step of storing data from the light detecting means and the displacement sensor means prior to the correlation of the data.

22. A method according to claim 17, wherein said step of irradiating primary light includes controlling a timing of an irradiation cycle for the light irradiation means.

23. A method according to claim 17, wherein said step of irradiating primary light includes steps of irradiating light from a plurality of light irradiation means, with at least two of said plurality of light irradiation means having different irradiation cycles.

24. A method according to claim 17, wherein said step of detecting secondary light comprises a step of detecting secondary light which is reflected from the specimen.

25. A method according to claim 17, wherein said step of irradiating primary light into the sample comprises a step of irradiating light having a wavelength which is between 400 nm and 10,000 nm.

26. A method according to claim 17, wherein said step of irradiating primary light comprises irradiating light from a plurality of light irradiating means, and wherein said step of detecting light includes a step of detecting light with a plurality of light detecting means, wherein each of the plurality of light irradiating means is paired with a corresponding one of the plurality of light detecting means, and wherein a distance between corresponding light irradiating means and light detecting means is approximately a same size or smaller than a size of an inhomogeneity in the sample which is to be measured.

27. A method according to claim 17, wherein said irradiating, detecting, and evaluating steps are repeated in order to evaluate time-related changes to the sample.

28. A method according to claim 17, wherein said step of detecting secondary light comprises a detection of intensity of the secondary light.

29. A method according to claim 17, wherein said step of detecting secondary light includes a step of detecting a degree of polarization of the secondary light.

30. A method according to claim 17, wherein said step of detecting the secondary light comprises a step of detecting a travel time of photons from the light irradiation means to the detecting means.

* * * * *